United States Patent
Zhang et al.

(10) Patent No.: US 12,180,242 B2
(45) Date of Patent: Dec. 31, 2024

(54) PHARMACEUTICAL CRYSTAL OF CONTEZOLID ACEFOSAMIL, PREPARATION METHOD THEREFOR, AND USES THEREOF

(71) Applicant: SHANGHAI MICURX PHARMACEUTICAL CO., LTD., Shanghai (CN)

(72) Inventors: Xueliang Zhang, Shanghai (CN); Xinghai Wang, Shanghai (CN); Jinqian Liu, Fremont, CA (US); Mikhail Fedorovich Gordeev, Castro Valley, CA (US)

(73) Assignee: SHANGHAI MICURX PHARMACEUTICAL CO., LTD, Shanghai (CN)

( * ) Notice: Subject to any disclaimer, the term of this patent is extended or adjusted under 35 U.S.C. 154(b) by 719 days.

(21) Appl. No.: 17/285,889

(22) PCT Filed: Sep. 29, 2019

(86) PCT No.: PCT/CN2019/109063
§ 371 (c)(1),
(2) Date: Apr. 15, 2021

(87) PCT Pub. No.: WO2020/078205
PCT Pub. Date: Apr. 23, 2020

(65) Prior Publication Data
US 2022/0153767 A1    May 19, 2022

(30) Foreign Application Priority Data
Oct. 15, 2018 (CN) .......................... 201811197435.4

(51) Int. Cl.
*C07F 9/6558* (2006.01)
*A61P 31/04* (2006.01)

(52) U.S. Cl.
CPC .......... *C07F 9/65583* (2013.01); *A61P 31/04* (2018.01); *C07B 2200/13* (2013.01)

(58) Field of Classification Search
CPC .................................................. C07B 2200/13
See application file for complete search history.

(56) References Cited

U.S. PATENT DOCUMENTS

| | | |
|---|---|---|
| 817,868 A | 4/1906 | Parsons |
| 8,163,940 B2 | 4/2012 | Pyo et al. |
| 8,178,683 B2 | 5/2012 | Gordeev |
| 9,382,276 B2 * | 7/2016 | Gordeev ............. C07F 9/65742 |
| 2006/0153913 A1 | 7/2006 | Yamane et al. |
| 2012/0190713 A1 | 7/2012 | Gordeev |
| 2020/0172507 A1 | 6/2020 | Takahashi et al. |

FOREIGN PATENT DOCUMENTS

| | | | |
|---|---|---|---|
| CN | 101720325 A | | 6/2010 |
| CN | 102206213 A | * | 10/2011 |
| CN | 105612166 A | | 5/2016 |
| JP | 2009-522351 A | | 6/2009 |
| KR | 1020070072786 A | | 7/2007 |
| WO | WO 99/32493 | | 7/1999 |
| WO | WO 2006/046623 A1 | | 5/2006 |
| WO | WO 2007/078050 A2 | | 7/2007 |
| WO | WO 2009/119785 A1 | | 10/2009 |
| WO | WO 2015/127316 A1 | | 8/2015 |
| WO | WO 2018/038255 A1 | | 3/2018 |

OTHER PUBLICATIONS

International Search Report and Written Opinion mailed on Jan. 2, 2020, for International Patent Application No. PCT/CN2019/109063; with English translation, 12 pages.
Communication Pursuant to Article 94(3) EPC dated Feb. 24, 2023 for European Patent Application No. 19872651.5; 4 pages.
International Search Report mailed on Jan. 2, 2020 for Application No. PCT/CN2019/109063; English translation, 2 pages.
Official Action dated May 12, 2023 forwarding examination report for Canadian Patent Application No. 3,116,783; 4 pages.
Pre-Grant Opposition for Indian Patent Application No. 202117021856 filed Oct. 11, 2022 (Part 1); 24 pages.
Pre-Grant Opposition for Indian Patent Application No. 202117021856 filed Oct. 11, 2022 (Part 2); 4 pages.
Lu, et al., "Polymorphism and crystallization of active pharmaceutical ingredients (APIs)", Current Medicinal Chemistry 2009; vol. 16, pp. 884-905.
Valente, et al., "Another glimpse over the salting-out assisted liquid-liquid extraction in acetonitrile/water mixtures", Journal of Chromatography A; Aug. 8, 2013, vol. 1308, pp. 58-62.
Byrn, et al: "Pharmaceutical solids: a strategic approach to regulatory considerations", Pharm. Res.; Jan. 1, 1995; vol. 12(7), pp. 945-954.
Caira, "Crystalline polymorphism of organic compounds", Topics in Current Chemistry; Jan. 1, 1998; vol. 198, pp. 163-208.
Hilfiker, et al: "Relevance of solid-state properties for pharmaceutical products", Polymorphism in the Pharmceutical Industry; Jan. 1, 2006; pp. 1-19; XP002528052.
Pre-Grant Opposition for Indian Patent Application No. 202117021856 filed Oct. 11, 2022 (Part 3); 126 pages; exhibits D1 through D5 marked for Controller and certified Sep. 12, 2022 under IN-DL86649117586742U; Form 26 dated Sep. 9, 2022.

* cited by examiner

*Primary Examiner* — Jeffrey S Lundgren
*Assistant Examiner* — Eric Tran
(74) *Attorney, Agent, or Firm* — Squire Patton Boggs (US) LLP

(57) ABSTRACT

The present invention relates to a pharmaceutical crystal of contezolid acefosamil, a preparation method therefor, and uses thereof. The present invention also relates to a crystal or crystal complex of formula I, wherein R is selected from hydrogen, sodium or a mixture thereof in any ratio.

13 Claims, 3 Drawing Sheets

PHARMACEUTICAL CRYSTAL OF CONTEZOLID ACEFOSAMIL, PREPARATION METHOD THEREFOR, AND USES THEREOF

CROSS-REFERENCE

This application is a 35 U.S.C. § 371 national phase filing of PCT/CN2019/109063 filed on Sep. 29, 2019, which claims the benefit of and priority to Chinese Patent Application 201811197435.4 filed on Oct. 15, 2018; both applications are incorporated herein by reference in their entireties.

TECHNICAL FIELD

The present invention relates to a pharmaceutical crystal of contezolid acefosamil, a preparation method therefor, and uses thereof.

BACKGROUND

Oxazolidinone compounds are a new class of synthetic compounds with inhibitory activity against various pathogenic microorganisms. Linezolid, the first drug of this class, has been approved for the treatment of Gram-positive infections. Linezolid has good antibacterial activity, but just as indicated in the "warnings" section of the prescription labeling of linezolid, myelosuppression and monoamine oxidase inhibition are major factors that limit the use of linezolid. Chinese Patent Publication No. CN105612166A discloses that Conzolid is a novel oxazolidinone compound with excellent safety features and good antibacterial activity.

In addition to the required antibacterial activity and safety, effective antibacterial drugs must have solubility and stability suitable for practical use. Chinese Patent Publication No. CN105612166A discloses a therapeutic water-soluble (O-carbonyl) phosphoramidate prodrug, which has good water solubility. However, the products obtained according to the preparation method of contezolid acefosamil provided by this publication are amorphous powders which are unstable and often lead to decomposition, wherein the X-ray powder diffraction analysis (FIG. 1) does not show any diffraction peak between 0~40° 2θ, no matter whether the products are obtained via laboratory's traditional operations such as extraction, evaporation under reduced pressure, or lyophilized by HPLC purification.

SUMMARY

In view of the above-mentioned problems, the present invention provides a crystal or crystal complex of contezolid acefosamil and a preparation method thereof, which has a significantly improved stability as compared to the amorphous powder, and thus can meet the requirements of pharmaceutical agents in clinical use.

In one aspect, the present invention relates to a crystal or crystal complex of formula I, wherein R is selected from hydrogen, sodium or a mixture thereof in any ratio. When R is selected from sodium, ONa and O⁻Na⁺ are equivalent.

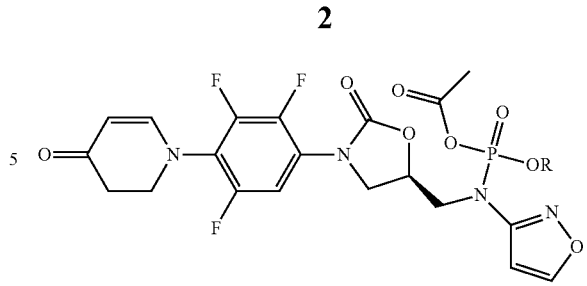

The crystal or crystal complex provided by the present invention greatly improves the stability of contezolid acefosamil, which is beneficial to the production and transportation of the drug, and the routine delivery of the drug to patients or mammals in need of treatment for bacterial infections, and thereby ensuring the clinical use of the new safe and effective oxazolidinone.

Preferably, wherein the crystal or crystal complex exhibits at least one diffraction peak at about 5.0-40°2θ in the X-ray powder diffraction pattern.

Preferably, wherein the crystal or crystal complex exhibits at least two diffraction peaks at about 20.0-25°2θ in the X-ray powder diffraction pattern.

Preferably, wherein the crystal or crystal complex exhibits a diffraction peak at about 20.0-21.0°2θ in the X-ray powder diffraction pattern.

Preferably, wherein the crystal or crystal complex exhibits a diffraction peak at about 23.0-24.0°2θ in the X-ray powder diffraction pattern.

Preferably, wherein crystal or crystal complex exhibits diffraction peaks at about 6.9°, 14.7°, 15.5°, 16.5°, 20.2°, 22.9°, 23.7° 2θ in the X-ray powder diffraction pattern.

Preferably, wherein the crystal or crystal complex has a melting point of 220±10° C.

Preferably, the crystal or crystal complex contains less than 6% of sodium by weight.

In the second aspect, the present invention provides a method for preparing the above-mentioned crystal or crystal complex, comprising the following steps:
(1) preparing the compound of formula I as a crude product;
(2) dissolving the compound of formula I as a crude product in a mixed solution of an organic solvent and water;
(3) optionally adding inorganic salt or organic solvent to the mixture, separating the product phase to remove part or all of the volatile substances, and optionally adding organic solvent, so as to obtain a crystal via crystallization;
(4) separating out the crystal of the compound of formula I.

Preferably, in step (2), wherein the organic solvent is selected from at least one of acetonitrile, acetone, methanol, ethanol, propanol, isopropanol, butanol, and tetrahydrofuran.

Preferably, in step (3), wherein the inorganic salt is selected from at least one of sodium chloride, sodium bromide, sodium iodide, sodium citrate, sodium dihydrogen phosphate, disodium hydrogen phosphate, sodium phosphate, sodium sulfate, sodium carbonate, sodium bicarbonate, sodium acetate and their hydrates.

Preferably, in step (3), wherein the organic solvent is selected from at least one of acetonitrile, acetone, methanol, ethanol, propanol, butanol, isopropanol, ethyl acetate, isopropyl acetate, methyl tert-butyl ether, and tetrahydrofuran.

In the third aspect, the present invention provides a use of the above-mentioned crystal or crystal complex for preparing an antibiotic medicine.

The present invention also provides a method for treating infections with above-mentioned crystal or crystal complex.

The present invention also provides a use of the above-mentioned preparation methods for preparing antibiotic agents.

In fourth aspect, the present invention provides a pharmaceutical composition comprising the above-mentioned crystal or crystal complex and a pharmaceutically acceptable carrier.

DETAILED DESCRIPTION

Figure 1:
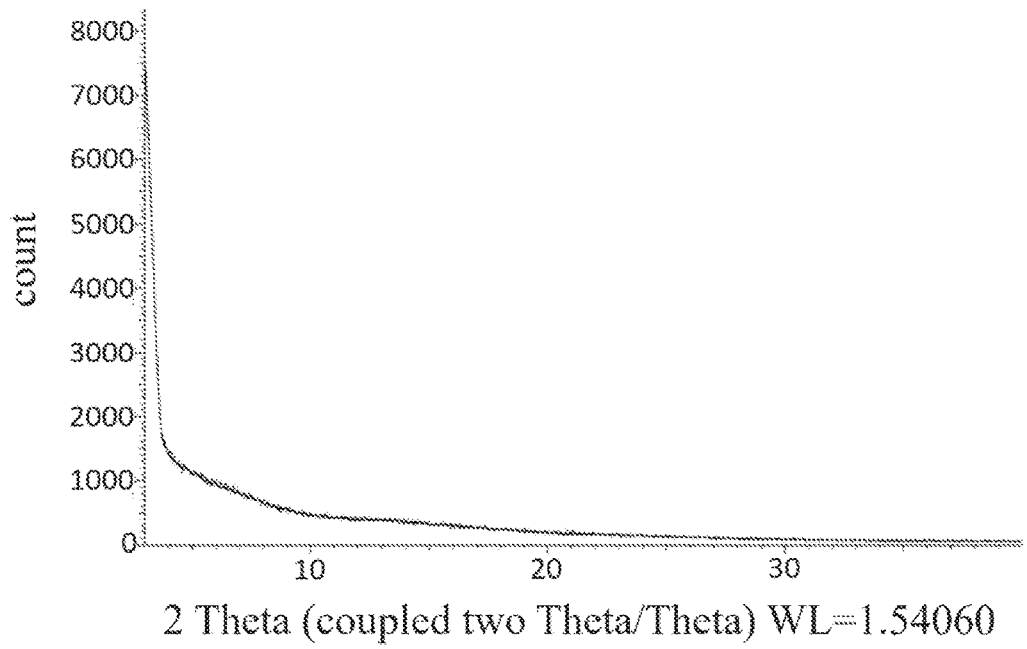
FIG. 1 shows an X-ray powder diffraction analysis of Product form 2 in Example 1.

Hereinafter, the present invention will be further described with the following examples. It should be understood that the following examples are used to explain this invention and do not mean to limit the scope of this invention.

The Terms

The term "about" when used in relation to the peak position of the X-ray powder diffraction pattern refers to the inherent variability of the peak, which depends on, for example, the calibration of the used equipment, the method for producing the polycrystal, the life of crystalline material, etc., depends on the instrument used. In this case, the measurement variability of the instrument is about ±0.2°2θ. Those skilled in the art can understand the use of "about" in this context.

The term "mammal" refers to all mammals including humans, livestock, and pets.

"Treating a disease" or "treatment of a disease" includes: (1) preventing the disease, i.e., causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The therapeutically effective amount will vary depending on the compound, the disease and its severity and the age, weight, etc., of the mammal to be treated.

The term "crystal complex" refers to a pharmaceutically acceptable crystal mixture containing a certain crystal. The crystal content can account for 50% to 90% of a product also including amorphous materials, moisture, and solvated organic solvents.

The term "complex" refers to a mixture or co-crystal.

The term "solvate" of a compound means that the compound contains a certain pharmaceutically acceptable solvent, whether chemically bound, such as a crystalline solvate, or remains, or as an additive, such as in a wet or lubricious solid.

The term "dissolving" refers to dispersing a solid into a liquid with or without stirring until a liquid is obtained, either a single phase, a layered heterogeneous solution, or a cloudy solution or suspension that is not completely transparent.

The term "volatile substances" refer to substances with low boiling points, especially organic solvents and water, such as acetonitrile, acetone, ethanol, isopropanol, ethyl acetate, hexane, cyclohexane, petroleum ether, methyl ethyl ketone, or their mixtures.

The term "salt" of a compound refers to a pharmaceutically acceptable salt with the desired pharmacological activity of the parent compound. Such salts include those formed as follows: when the acid protons in the parent compound are replaced by metal ions, such as alkali metal ions, alkaline earth metal ions, zinc or aluminum ions; or when the acid protons in the parent compound are coordinated with organic bases, such as glutamic acid, lysine, ethanolamine, diethanolamine, triethanolamine, trimethylaminomethane, N-methylglucamine and the like.

The compounds disclosed herein are generally named according to the IUPAC or CAS nomenclature system.

The crystal or crystal complex.

Due to the specificity of N-phosphoryl and -acetyl phosphoric acid in its structure, contezolid acefosamil is unstable under some conditions as a prodrug, and conventional heating and dissolving, cooling and crystallization methods often lead to decomposition. A novel crystal or crystal complex of contezolid acefosamil (formula I) is disclosed herein. The crystal is stable at room temperature, and the nature of the crystal is obvious.

In formula I, R is selected from hydrogen, sodium or a mixture thereof in any ratio. When R is sodium, ONa and $O^-Na^+$ are equivalent.

In some embodiments, the crystal or crystal complex is a mixture of formula I with R=hydrogen and R=sodium each in any amount from 0 to 50%.

In some embodiments, the content of the compound of formula I with R=hydrogen is less than 5% (by weight). This can improve the crystallinity of the compound.

In some embodiments, the content of sodium in the crystal or crystal complex is from 1 to 10% (by weight), more preferably from 3.2 to 6% (by weight). This can improve the crystallinity of the compound.

Figure 2:
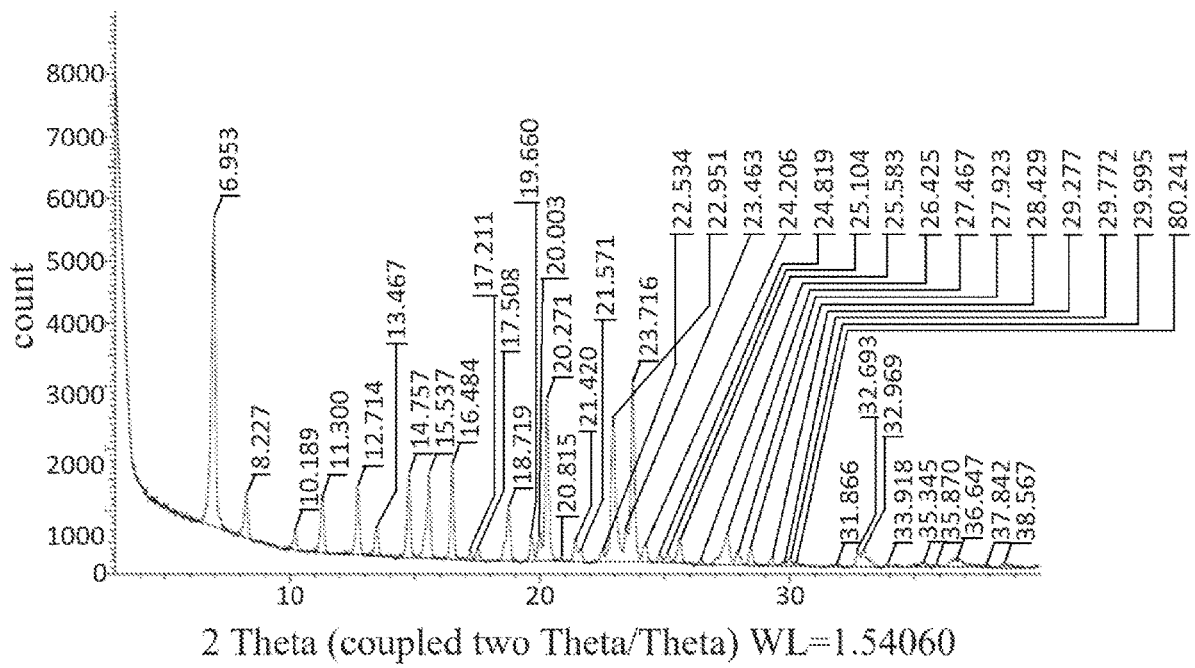
FIG. 2 shows an X-ray powder diffraction analysis of Product 3 form (crystal) in Example 1.

The crystal or crystal complex of the present disclosure exhibits more than one sharp diffraction peak between 0-40°2θ in the X-ray powder diffraction analysis (XRPD) (FIG. 2).

In some embodiments, the crystal or crystal complex exhibits at least one diffraction peak at about 5.0~40°2θ in the X-ray powder diffraction pattern.

In some embodiments, the crystal or crystal complex exhibits at least two diffraction peaks at about 20.0~25°2θ in the X-ray powder diffraction pattern.

In some embodiments, the crystal or crystal complex exhibits at least one sharp diffraction peak at about 6.0~8.0°2θ in the X-ray powder diffraction pattern.

In some embodiments, the crystal or crystal complex exhibits diffraction peaks at about 20.0~21.0°2θ in the X-ray powder diffraction pattern.

In some embodiments, the crystal or crystal complex exhibits diffraction peaks at about 23.0~24.0°2θ in the X-ray powder diffraction pattern.

The crystal or crystal complex of the present disclosure greatly improves the stability of contezolid acefosamil, for example, enabling it to be substantially free of decomposition at room temperature for 24 hours. The increase in the stability of the sample also proves the formation of the crystal or crystal complex.

In some embodiments, the crystal or crystal complex has a melting point of 220±10° C.

The crystal or crystal complex of the present disclosure may contain one crystal form, and may also contain multiple crystal forms.

The crystal or crystal complex of the present disclosure may contain one or more crystal forms or a mixture thereof Preparation The preparation method of the above-mentioned crystal or crystal complex is also disclosed herein. In some embodiments, the compound of formula I (contezolid acefosamil of formula I as a crude product) is dissolved in a biphasic solution of an organic solvent and water; inorganic salt is added, and then the product phase is separated to remove part or all of the volatile substances, and organic solvent is added, so as to obtain a crystal via crystallization. Contezolid acefosamil of formula I as a crude product can be prepared by the method disclosed in CN105612166A.

The volume ratio of organic solvent and water is preferably 1:9 to 4:6.

In some embodiments, the organic solvent may be selected from at least one of acetonitrile, acetone, methanol, ethanol, propanol, isopropanol, butanol, ethyl acetate, isopropyl acetate, n-heptane, hexane, cyclohexane, petroleum ether, methyl ethyl ketone, and tetrahydrofuran.

In a more preferred embodiment, the organic solvent may be selected from at least one of acetonitrile, ethanol, butanol, isopropanol, acetone, methyl ethyl ketone, and tetrahydrofuran.

The method of dissolving the compound of formula I in the mixed solution of an organic solvent and water may be dissolving by stirring.

Optionally, an inorganic salt is also added to the mixed solution of organic solvent and water. The inorganic salt may be, for example, at least one of sodium chloride, sodium bromide, sodium iodide, sodium citrate, sodium dihydrogen phosphate, disodium hydrogen phosphate, sodium phosphate, sodium sulfate, sodium carbonate, sodium bicarbonate, sodium acetate and hydrates thereof.

During the crystallization process, the concentration of the crystallization solution, the rate of crystallization and temperature can be controlled.

Optionally, part or all of the volatile substances in the product phase such as organic solvent and water is removed. It can be removed by, for example, azeotropic distillation, vacuum distillation, and the like.

Optionally, a second organic solvent is added to the product phase for crystallization. The second organic solvent may be selected from at least one of acetonitrile, acetone, methanol, ethanol, propanol, isopropanol, butanol, ethyl acetate, isopropyl acetate, methyl tert-butyl ether, and tetrahydrofuran. The quantity of the second organic solvent added can be 2-50 times the weight of the substrate.

Optionally, the product phase is cooled to about −30° C. to about 20° C. for crystallization.

After crystallization, the product can be separated out to obtain crystal or crystal complex. Further, the obtained crystal or crystal complex can be dried.

In some embodiments, the crystal is physically separated or filtered.

In some embodiments, the separated crystal is vacuum dried to obtain crystal or crystal complex. The temperature during vacuum drying can be about 15° C. to about 80° C., preferably about 20° C. to about 50° C.

In some embodiments, a method of treating a mammalian microbial infection or bacterial infection with the above-mentioned crystal or crystal complex is provided, comprising: administering a therapeutically effective amount of the crystal or crystal complex to the mammal. The crystal or crystal complex can be administered to mammals by oral, parenteral, transdermal, topical, rectal or intranasal routes in the form of a pharmaceutical composition. In some embodiments or in any embodiment, the microorganisms are Gram-positive microorganisms in the method. Therefore, the crystal or crystal complex of the present invention is a useful antimicrobial agent, and may be effective against many human and animal pathogens, including Gram-positive aerobic bacteria such as multi-resistant *Staphylococcus aureus*, Enterococci, and Streptococci, as well as anaerobic microorganisms such as *Bacteroides* and *Clostridium*, and acid-fast microorganisms such as *Mycobacterium tuberculosis* and *Mycobacterium avium*.

The crystal or crystal complex provided in the present disclosure can be conveniently added to the pharmaceutical composition in a conventional manner. The pharmaceutical composition or medicament may further comprise a pharmaceutically acceptable diluent, excipient, disintegrant, lubricant or carrier.

Pharmaceutical compositions containing the crystal or crystal complex of the present disclosure are prepared and the pharmaceutically acceptable carrier can be either solid or liquid. Solid form preparations include powders, tablets, dispersible granules, capsules, cachets, and suppositories. Tablets, powders, cachets, and capsules can be used as solid dosage forms suitable for oral administration. Illustrative examples of pharmaceutically acceptable formulations and methods for preparing certain pharmaceutical compositions are described, for example, in "The Science and Practice of Pharmacy," edited by A. Gennaro, Lippincott Williams & Wilkins, Baltimore, Md. (Md., 2000).

In some embodiments, the crystal or crystal complex can be made into various pharmaceutically acceptable compositions such as water, a D5W injection solution or other tablets for treating or preventing various infections.

Hereinafter, the present invention will be further described with the following examples. It should be understood that the following examples are used to explain this invention but do not mean to limit the scope of this invention. Any non-essential improvements and modifications made by a person skilled in the art based on this invention all fall into the protection scope of this invention. The specific process parameters below are only exemplary, and a person skilled in the art can choose proper values within an appropriate range according to the description, and are not restricted to the specific values shown below.

The test methods in the following embodiments are as follows: X-ray powder diffraction analysis: Panalytical's XPERT-3 X-ray diffractometer was used. Approximately 10 mg samples were spread evenly on a sample tray of monocrystalline silicon XRPD tests were performed with the parameters described below:

| Start Position [°2Th.]: 3.0121 | End Position [°2Th.]: 39.9870 |
| Step Size [°2Th.]: 0.0163 | Scan Step Time [s]: 46.665 |
| K-Alpha-1 [Å]: 1.54060 | K-Alpha-2 [Å]: 1.54443 |
| Generator Settings: 40 mA, 45 kV | |

DSC analysis: TA Q2000 differential scanning calorimeter was used to perform DSC analysis with the following parameters:

| Sample tray | Aluminum plate, gland |
|---|---|
| temperature range/° C. | 25-350° C. |
| Scan speed | 10 |
| Protective gas | Nitrogen |

Example 1

Synthetic Route:

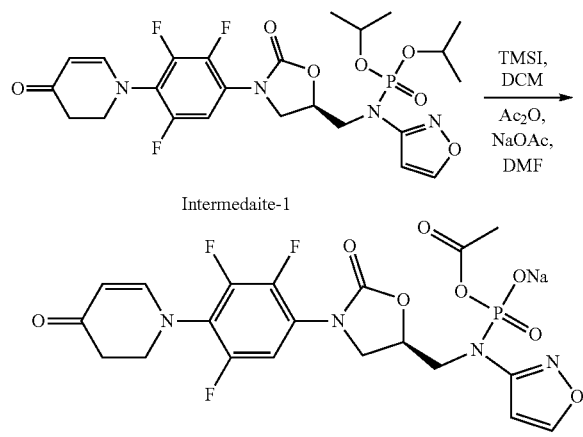

Example 1

Compound of Example 1: Under nitrogen protection, trimethylsilyl iodide (14.4 g) was added dropwise to a solution of intermediate 1 (10.5 g, prepared according to the method of CN105612166A, Intermediate 2) in DCM (105 mL) at 0-10° C., and stirred at room temperature for 2 hours. The reaction solution was concentrated under reduced pressure, and the residue was rinsed with methyl tert-butyl ether (100 mL), filtered, and dried in vacuo. The resulting product was redissolved in DMSO/MeCN (10.5 mL/105 mL), to which NaOAc (36.7 g) and $Ac_2O$ (5.9 g) were added, and the mixture was stirred for 1 hour. MTBE (700 mL) was added, and the mixture was stirred, filtered, and the filter residue was dried in vacuo to obtain crude compound of Example 1.

Figure 3:
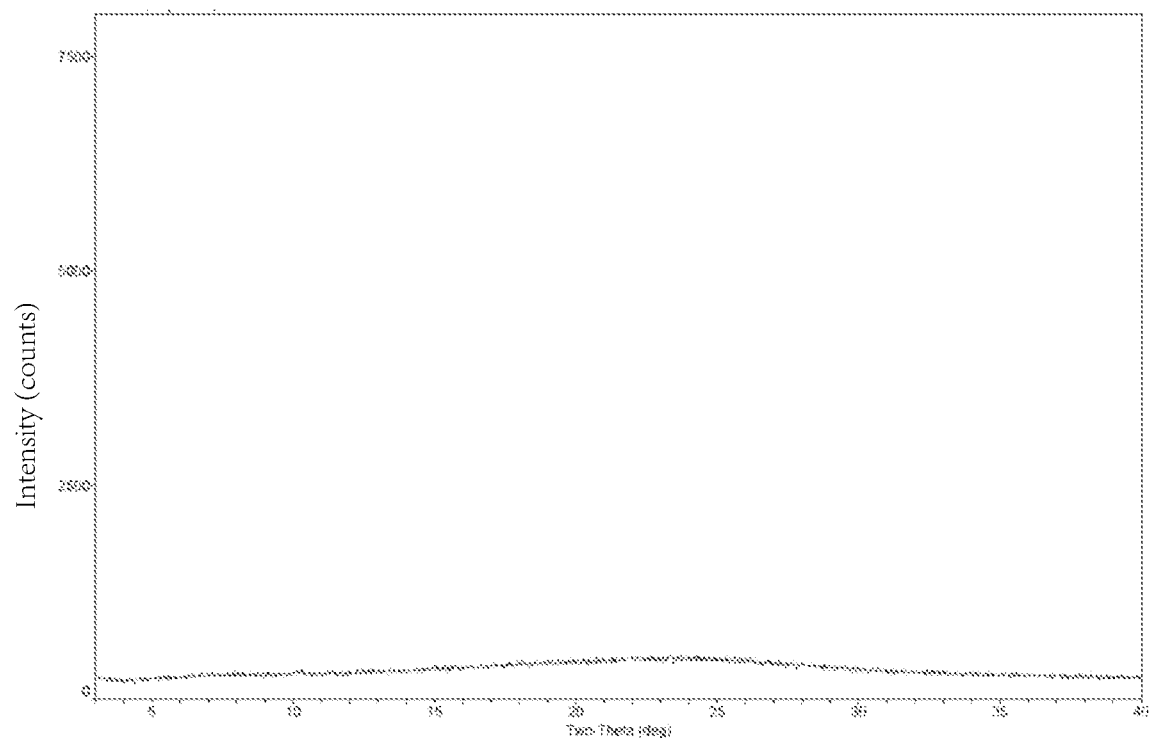
FIG. 3 shows an X-ray powder diffraction analysis of product 1 form in Example 1.

Example 1 Product Form 1: The crude product of Example 1 was stirred in 5% EtOH/DCM (1000 mL), and filtered, and the mother liquor was concentrated under reduced pressure. The residue was slurried with ethyl acetate:methyl tert-butyl ether (3:1, 300 mL). Filtration, washing (the residue was washed with ethyl acetate:methyl tert-butyl ether), and vacuum drying gave a yellow solid as product form 1. MS: 531 [M+H]. The product X-ray powder diffraction analysis of the product was shown in FIG. 3.

Example 1 Product Form 2: The crude product of Example 1 was dissolved in water and purified by reverse phase HPLC (C18) gradient. The mobile phase was water and acetonitrile. The fractions containing Example 1 were collected. Lyophilization gave a white solid as product form 2. MS: 531 [M+H]. The product X-ray powder diffraction analysis of the product was shown in FIG. 1.

Crystal or crystal complex of the product of Example 1 (product form 3): The crude product of Example 1 (146 g) was dissolved in water (582 mL) and acetonitrile (169 mL) at room temperature, and dissolved by stirring, and sodium dihydrogen phosphate dehydrate (349 g) was added and dissolved by stirring. The product phase was separated and concentrated under reduced pressure until there was no obvious fraction, and then acetone (550 mL) was added to dissolve the residue. The resulting mixture was cooled, and stirred for crystallization followed by filtration and vacuum drying to obtain a white solid with a sodium content of 4.3%. The product X-ray powder diffraction analysis of the product was shown in FIG. 2, and the DSC analysis result was shown in FIG. 4.

Test and Application

In the early development and research of contezolid acefosamil, the product obtained via laboratory's traditional operations such as extraction, and evaporation under reduced pressure were unstable in storage at room temperature. Even the product lyophilized by HPLC purification was not stable enough, while X-ray powder diffraction showed no diffraction peaks. Surprisingly, for the product obtained by the preparation method of the present invention, the X-ray powder diffraction analysis showed many sharp diffraction peaks between 0-40°2θ, and the analysis result of the differential scanning calorimetry (DSC) also showed a narrow melting range, indicating the crystal features. More importantly, the resulting crystalline product had better stability than amorphous powder. The detailed data are as follows.

The X-ray powder diffraction data of the product obtained by the preparation method of the present invention are shown in Table 1 and the diffraction analysis chart is shown in FIG. 2.

Table 1 shows main peaks of crystal X-ray powder diffraction of the present invention.

| angle (2θ°) | relative strength (%) |
|---|---|
| 6.9 | 100 |
| 14.7 | 29.5 |
| 15.5 | 29.3 |
| 16.5 | 31.2 |
| 20.2 | 50.8 |
| 22.9 | 42.1 |
| 23.7 | 54.4 |

It can be seen from Table 1 and FIG. 2 that the product has more than one distinct sharp peak. This shows that the product has obvious crystallographic features that reflect X-rays on the crystal surface. It is a new crystal that cannot be obtained by routine methods of manipulation by solvent recrystallization, HPLC purification, or lyophilization.

The stability of the crystal of the present invention: The purity change (stability) of the two samples at room temperature for nine months was determined by the HPLC method. One was the product obtained by HPLC purification lyophilization (product form 2 in Example 1); the other was the product (product form 3 in Example 1) obtained by the method which was provided by the present invention for preparing the crystal. The results are shown in Table 2.

Table 2 shows stability of the product for nine months (HPLC purity, %).

| | Time (month) | | | | |
|---|---|---|---|---|---|
| | 0 | 1 | 2 | 3 | 9 |
| Product form 2 | 97.29 | 94.27 | 92.99 | 91.27 | 83.21 |
| Product form 3 | 97.54 | 96.61 | 96.77 | 96.84 | 95.81 |

It can be seen from Table 2 that both products decompose slowly. Product form 3 (crystal) is significantly more stable than product form 2 (amorphous powder) at room temperature, and more pronounced at nine months (95.81% and 83.21%). The large increase in the stability of the sample also confirms that the existence of the crystal or crystal complex.

Figure 5:
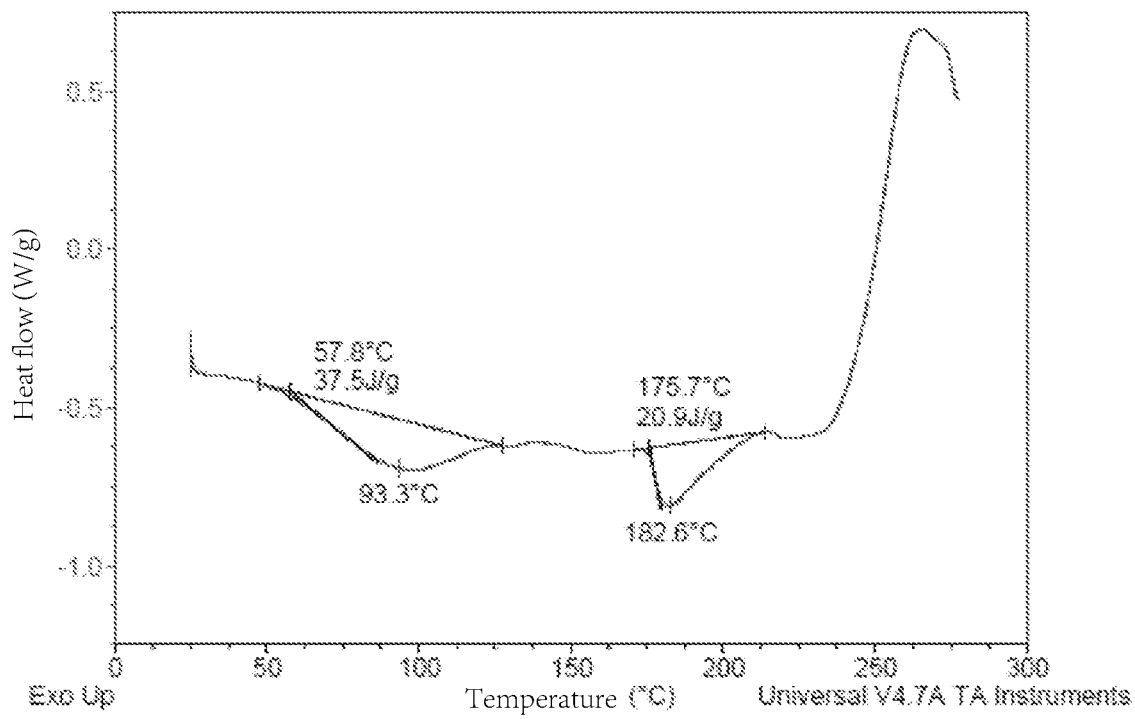
FIG. 5 shows a differential thermal scanning analysis of the product obtained by re-dissolving the crystal in water and then being lyophilized.

On the other hand, the analysis results of differential scanning calorimetry (DSC) also confirms the existence of crystalline material. FIG. 5 is a DSC analysis diagram of the crystal (product form 3 in Example 1) that was re-dissolved in water and lyophilized.

Figure 4:
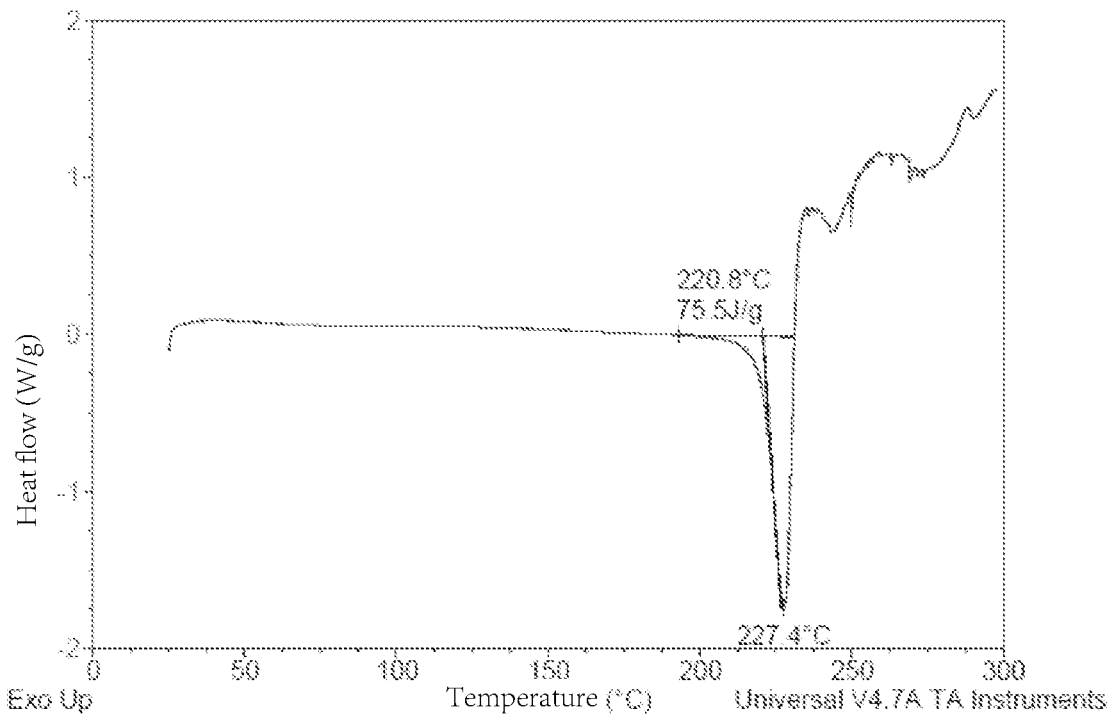
FIG. 4 shows a differential thermal scanning analysis of Product 3 form (crystal) in Example 1.

In comparison with the DSC analysis diagram of the crystal in FIG. 4, the product obviously has a narrow melting range indicating a crystal feature of a single crystal or of a crystallized complex with a crystal dominant component.

The method for preparing the crystal form of the present invention is unique and cannot be achieved by traditional crystallizing operations (heating solvent and dissolution, cooling and crystallization). For example, acetonitrile, one of the solvents used for extraction in some embodiments, is not used in general extraction operations.

The crystal or crystal complex of the oxazolidinone compounds of the present invention shows effective in vivo activity against a variety of microorganisms, including Gram-positive microorganisms. In order to determine the effective therapeutic activity of the crystal or crystal complex of the present invention, a mouse peritonitis infection model according to the general procedure described by Marra et al., Current Protocols in Pharmacology (2005), 13A.4.1-13A.4.13 was used as the test method.

In this infection model, pathogenic *Staphylococcus aureus* strain SAU1018 was used, and an intravenous injection of a saline solution containing these crystals suitable for clinical or therapeutic use was administered to infected animals, showing high in vivo activity. The $ED_{50}$ value (effective dose for 50% animal survival in the test) of the crystal or crystal complex is 10 mg/kg.

The crystal or crystal complex of the present invention can also be administered using a convenient oral route. When administered orally to the above-mentioned mouse model animals infected with *Staphylococcus aureus*, the compound showed high antibacterial efficacy, and its $ED_{50}$ value was about 8 mg/kg.

Accordingly, the crystals of the present invention or substance that contains the crystal and composition thereof of the present invention possess useful antibacterial activity. Therefore, the crystals of the present invention are useful antimicrobial agents and may be effective against many human and animal pathogens, including Gram-positive aerobic bacteria such as multi-resistant *Staphylococcus aureus*, Enterococci, Streptococci, and anaerobic microorganisms such as *Bacteroides* and *Clostridium*, and acid-fast microorganisms such as *Mycobacterium tuberculosis* and *Mycobacterium avium*. These pharmaceutical compositions can be administered by a variety of different routes such as intravenous injection, oral administration, parenteral administration, transdermal administration, topical administration, rectal administration and intranasal administration.

The various aspects described above are brief descriptions of the present invention. After reading the foregoing specification, a person with ordinary skills in the art can make changes, equivalent substitutions and other types of changes to the invention proposed herein. However, the present invention is not limited to the statements and examples described herein. Many modifications and variations of the crystal or crystal complex of the present invention and the preparation method thereof can be realized without departing from its spirit and scope, as will be obvious to those skilled in the art. Functionally equivalent methods within the scope of the present invention, in addition to those listed here, will also be apparent to those skilled in the art based on the foregoing description. It is understood that the present invention is not limited to certain methods, solvents, salts, operating sequences, process conditions and other factors that can of course vary. It can also be understood that the terms used herein are for the purpose of describing particular aspects only and are not intended as limiting conditions. Therefore, the description should be regarded as exemplary.

The invention claimed is:

1. A crystal or crystal complex of a compound of formula I, wherein R is sodium,

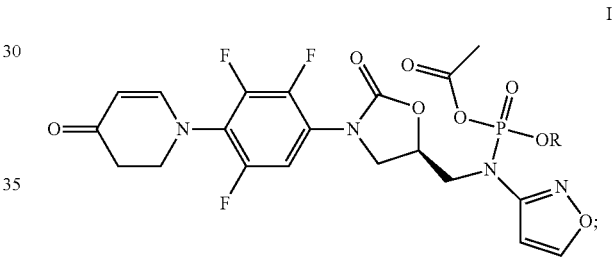

wherein an X-ray powder diffraction (XRPD) pattern for the crystal or crystal complex of the compound of formula I exhibits diffraction peaks at least at the following 2θ positions: 6.9°, 14.7°, 15.5°, 16.5°, 20.2°, 22.9°, and 23.7°2θ, wherein the XRPD pattern is obtained with K-Alpha radiation having a wavelength of 1.54 Å, and wherein the 2θ position variation is ±0.2.

2. The crystal or crystal complex of claim 1, wherein the crystal compound or crystal complex exhibits at least one diffraction peak selected from about 6.0~8.0°2θ with a relative strength greater than all other diffraction peaks in its X-ray powder diffraction (XRPD) pattern, wherein the XRPD pattern is obtained with K-Alpha radiation having a wavelength of 1.54 Å.

3. The crystal or crystal complex of claim 2, wherein the crystal compound or crystal complex exhibits a diffraction peak selected from about 23.0-24.0°2θ with a relative strength greater than all but the at least one diffraction peak selected from about 6.0~8.0°2θ in its X-ray powder diffraction (XRPD) pattern, wherein the XRPD pattern is obtained with K-Alpha radiation having a wavelength of 1.54 Å.

4. The crystal or crystal complex of claim 1, wherein the crystal or crystal complex has a melting point of 220±10° C.

5. A method for preparing the crystal or crystal complex according to claim 1, comprising the following steps:
(1) preparing a compound of formula I

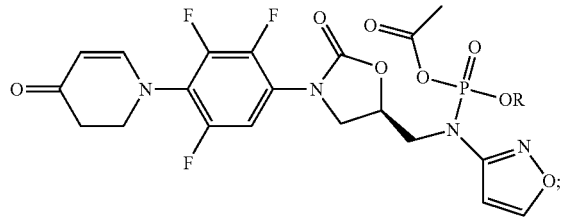

(2) dissolving the compound of formula I as a crude product in a mixed solution of an organic solvent and water;
(3) adding inorganic salt or organic solvent to the mixture, separating the product phase to remove part or all of the volatile substances, and adding organic solvent, so as to obtain a crystal via crystallization; and
(4) separating out the crystals of the compound of formula I.

6. The method of claim 5, wherein in step (2), the organic solvent is selected from at least one of acetonitrile, acetone, methanol, ethanol, propanol, isopropanol, butanol, and tetrahydrofuran.

7. The method of claim 5, wherein in step (3), the inorganic salt is selected from at least one of sodium chloride, sodium bromide, sodium iodide, sodium citrate, sodium dihydrogen phosphate, disodium hydrogen phosphate, sodium phosphate, sodium sulfate, sodium carbonate, sodium bicarbonate, sodium acetate and their hydrates.

8. The method of claim 5, wherein in step (3), the organic solvent is selected from at least one of acetonitrile, acetone, methanol, ethanol, propanol, isopropanol, butanol, ethyl acetate, isopropyl acetate, methyl tert-butyl ether, and tetrahydrofuran.

9. A method of treating a microbial infection in a mammal, comprising administering a therapeutically effective amount of the crystal or crystal complex of claim 1 to the mammal.

10. A pharmaceutical composition comprising the crystal or crystal complex according to claim 1 and a pharmaceutically acceptable carrier.

11. The method of claim 9, wherein the therapeutically effective amount of the crystal or crystal complex is administered in a pharmaceutical composition which further comprises a pharmaceutically acceptable carrier.

12. The method of claim 9, wherein the method is for treating a bacterial infection.

13. The method of claim 12, wherein the bacterial infection is a Gram-positive bacterial infection.

* * * * *